United States Patent  
Tanaka et al.

(10) Patent No.: US 10,018,552 B2
(45) Date of Patent: Jul. 10, 2018

(54) PARTICLE ANALYSIS APPARATUS, OBSERVATION APPARATUS, PARTICLE ANALYSIS PROGRAM AND PARTICLE ANALYSIS METHOD

(71) Applicant: NIKON CORPORATION, Minato-ku, Tokyo (JP)

(72) Inventors: Daishi Tanaka, Konosu (JP); Hisao Osawa, Kashiwa (JP); Kuno Suzuki, Iruma-gun (JP)

(73) Assignee: Nikon Corporation, Minato-Ku, Tokyo (JP)

( * ) Notice: Subject to any disclaimer, the term of this patent is extended or adjusted under 35 U.S.C. 154(b) by 83 days.

(21) Appl. No.: 15/210,158

(22) Filed: Jul. 14, 2016

(65) Prior Publication Data

US 2016/0320289 A1 Nov. 3, 2016

Related U.S. Application Data

(63) Continuation of application No. PCT/JP2015/050613, filed on Jan. 13, 2015.

(30) Foreign Application Priority Data

Jan. 17, 2014 (JP) .................................. 2014-007158

(51) Int. Cl.
  *G01N 15/00* (2006.01)
  *G01N 15/14* (2006.01)
  (Continued)

(52) U.S. Cl.
  CPC ......... *G01N 15/1459* (2013.01); *G01N 15/00* (2013.01); *G01N 15/1463* (2013.01);
  (Continued)

(58) Field of Classification Search
  CPC combination set(s) only.
  See application file for complete search history.

(56) References Cited

U.S. PATENT DOCUMENTS 4,351,709 A * 9/1982 Goetz .............. G01N 27/44721
  204/549
6,150,089 A * 11/2000 Schwartz ................. C12Q 1/68
  204/450
(Continued)

FOREIGN PATENT DOCUMENTS

JP 2003-270261 A 9/2003
JP 2005-164560 A 6/2005
(Continued)

OTHER PUBLICATIONS

International Search Report and Written Opinion of PCT/JP2015/050613 dated Feb. 10, 2015 with English translation of Written Opinion; 15 pages.

*Primary Examiner* — Tsung-Yin Tsai
(74) *Attorney, Agent, or Firm* — Squire Patton Boggs (US) LLP

(57) ABSTRACT

A particle analysis apparatus includes: an acquisition unit that acquires a plurality of images each captured at a different time in each of which a particle moving in a predetermined direction in a medium is imaged; and a determination unit that determines, based on a movement amount of a particle due to Brownian motion in the medium, whether or not an image of a first particle included in an image captured at a first time of the plurality of images acquired by the acquisition unit and an image of a second particle included in an image captured at a second time which is different from the first time of the plurality of images acquired by the acquisition unit are images indicating the same particle.

17 Claims, 11 Drawing Sheets

(51) Int. Cl.
 *G01N 21/53* (2006.01)
 *G01N 15/10* (2006.01)

(52) U.S. Cl.
 CPC ......... *G01N 21/53* (2013.01); *G01N 15/1468* (2013.01); *G01N 2015/0003* (2013.01); *G01N 2015/0038* (2013.01); *G01N 2015/0065* (2013.01); *G01N 2015/1075* (2013.01); *G01N 2201/12* (2013.01)

(56) References Cited

U.S. PATENT DOCUMENTS

| | | | | |
|---|---|---|---|---|
| 6,280,960 | B1* | 8/2001 | Carr | G01N 15/1463 356/244 |
| 7,605,919 | B2* | 10/2009 | Oma | G01N 15/1463 356/339 |
| 2003/0020910 | A1* | 1/2003 | Peterson | G01N 15/1459 356/338 |
| 2006/0160157 | A1* | 7/2006 | Zuckerman | A61K 51/0476 435/7.23 |
| 2007/0059763 | A1* | 3/2007 | Okano | G01N 33/566 435/7.1 |
| 2009/0238413 | A1 | 9/2009 | Ikeda et al. | |
| 2010/0002908 | A1* | 1/2010 | Miyamoto | B60R 1/00 382/103 |
| 2011/0036719 | A1* | 2/2011 | Neyts | G01N 15/1031 204/549 |
| 2011/0155650 | A1* | 6/2011 | McNeil-Watson | G01N 27/44721 209/155 |
| 2011/0170659 | A1* | 7/2011 | Ohzu | G01N 23/223 378/50 |
| 2012/0251618 | A1 | 10/2012 | Schrum et al. | |
| 2012/0293797 | A1* | 11/2012 | Braeckmans | G01N 21/05 356/246 |
| 2013/0273544 | A1* | 10/2013 | Vlassov | G01N 1/34 435/6.12 |
| 2016/0238530 | A1* | 8/2016 | Furuya | G01N 21/645 |

FOREIGN PATENT DOCUMENTS

| | | |
|---|---|---|
| JP | 2007-322329 A | 12/2007 |
| JP | 2009-229103 A | 10/2009 |

\* cited by examiner

FIG. 7

| | | t0 | t1 | t2 | ... | t48 | t49 | t50 |
|---|---|---|---|---|---|---|---|---|
| P1 | X | x1 | x1' | ⋮ | ⋮ | | | |
| | Y | y1 | y1 | ⋮ | ⋮ | | | |
| | I | l1 | l1 | ⋮ | ⋮ | | | |
| | S | s1 | s1 | ⋮ | ⋮ | | | |
| P2 | X | x2 | x2' | ⋮ | ⋮ | | | |
| | Y | y2 | y2 | ⋮ | ⋮ | | | |
| | I | l2 | l2 | ⋮ | ⋮ | | | |
| | S | s2 | s2 | ⋮ | ⋮ | | | |
| ... | | | | | | | | |
| P100 | X | ⋮ | ⋮ | ⋮ | ⋮ | x100 | | |
| | Y | ⋮ | ⋮ | ⋮ | ⋮ | y100 | | |
| | I | ⋮ | ⋮ | ⋮ | ⋮ | l100 | | |
| | S | ⋮ | ⋮ | ⋮ | ⋮ | s100 | | |

PARTICLE ANALYSIS APPARATUS, OBSERVATION APPARATUS, PARTICLE ANALYSIS PROGRAM AND PARTICLE ANALYSIS METHOD

CROSS-REFERENCE TO RELATED APPLICATION

This is a Continuation application of International Application No. PCT/JP2015/050613, filed on Jan. 13, 2015, which claims priority on Japanese Patent Application No. 2014-7158, filed on Jan. 17, 2014. The contents of the aforementioned applications are incorporated herein by reference.

BACKGROUND

Field of the Invention

The present invention relates to a particle analysis apparatus, an observation apparatus, a particle analysis program and a particle analysis method.

Background

Apparatuses are known in which an image of a particle moving in a medium is captured according to microscope observation under dark-field illumination, and the captured image is processed to thereby obtain the number of particles and a movement speed of the particle (for example, refer to Japanese Unexamined Patent Application, First Publication No. 2009-229103). In such apparatuses, the movement path of a particle is traced based on a plurality of images captured at a different timing to thereby obtain the number of particles and the movement speed of the particle.

SUMMARY

However, for example, according to the technique disclosed in Japanese Unexamined Patent Application, First Publication No. 2009-229103, there may be a case in which the movement path of a particle cannot be traced when the particle is moved out of the field of view of the microscope, and in this case, it is impossible to reduce the measurement error of the number of particles, the movement speed of the particle, and the like.

An aspect of the present invention provides a particle analysis apparatus, an observation apparatus, a particle analysis program and a particle analysis method capable of reducing the measurement error of a particle.

An aspect of the present invention is a particle analysis apparatus including: an acquisition unit that acquires a plurality of images each captured at a different time in each of which a particle moving in a predetermined direction in a medium is imaged; and a determination unit that determines, based on a movement amount of a particle due to Brownian motion in the medium, whether or not an image of a first particle included in an image captured at a first time of the plurality of images acquired by the acquisition unit and an image of a second particle included in an image captured at a second time which is different from the first time of the plurality of images acquired by the acquisition unit are images indicating the same particle.

Further, an aspect of the present invention is an observation apparatus including: the above particle analysis apparatus; and an imaging unit that captures an image of scattered light arising from a particle in the medium due to irradiated light at each one of a plurality of different times.

Further, an aspect of the present invention is a particle analysis program for causing a computer to execute (a) acquiring a plurality of images each captured at a different time in each of which a particle moving in a predetermined direction in a medium is imaged and (b) determining, based on a movement amount of a particle due to Brownian motion in the medium, whether or not an image of a first particle captured at a first time of the plurality of images acquired in (a) and an image of a second particle captured at a second time which is different from the first time of the plurality of images acquired in (a) are images indicating the same particle.

Further, an aspect of the present invention is a particle analysis method including (a) acquiring a plurality of images each captured at a different time in each of which a particle moving in a predetermined direction in a medium is imaged and (b) determining, based on a movement amount of a particle due to Brownian motion in the medium, whether or not an image of a first particle captured at a first time of the plurality of images acquired in (a) and an image of a second particle captured at a second time which is different from the first time of the plurality of images acquired in (a) are images indicating the same particle.

According to an aspect of the present invention, it is possible to reduce the measurement error of a particle.

BRIEF DESCRIPTION OF DRAWINGS

FIG. 7 is a view showing an example of a particle list stored in a storage unit of the present embodiment.

DESCRIPTION OF THE EMBODIMENTS

[First Embodiment]

Hereinafter, an embodiment of the present invention will be described with reference to the drawings.

Figure 1:
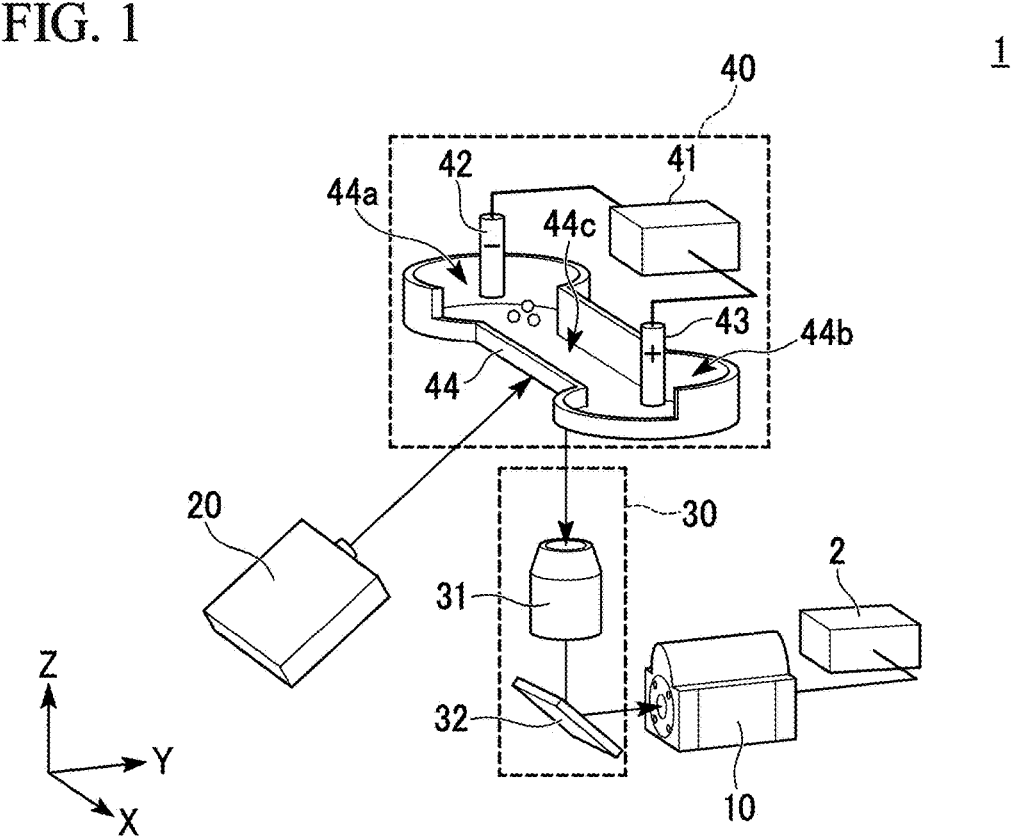
FIG. 1 is a schematic view showing an example of an exterior configuration of an observation apparatus according to a first embodiment of the present invention.

FIG. 1 is a schematic view showing an example of an exterior configuration of an observation apparatus 1 according to a first embodiment of the present invention. The observation apparatus 1 includes an electrophoresis apparatus 40.

Hereinafter, in the present embodiment, a configuration of the observation apparatus 1 is described using an XYZ orthogonal coordinate system.

In the XYZ orthogonal coordinate system, the vertical direction is a Z direction, the migration direction by the electrophoresis apparatus 40 is an X direction, and the direction orthogonal to the X direction and the Z direction is a Y direction.

The electrophoresis apparatus 40 includes a power source 41, a negative electrode 42, a positive electrode 43, and an electrophoresis cell 44. The electrophoresis cell 44 includes a reservoir 44a at a first end part in the X direction. The electrophoresis cell 44 includes a reservoir 44b at a second end part in the X direction. Further, the electrophoresis cell 44 includes a flow path 44c that connects the reservoir 44a and the reservoir 44b. As an example of the size of the flow path 44c, the length in the X direction is 1000 [μm], the width in the Y direction is 200 [μm], and the height in the Z direction is 50 [μm]. The numerical values are examples, and the size of the flow path 44c is not limited thereto. The negative electrode 42 is configured, for example, by a metal such as platinum and is arranged at the reservoir 44a located at an end (first end part) in the −X direction of the electrophoresis cell 44. The positive electrode 43 is configured, for example, by a metal such as platinum similarly to the negative electrode 42 and is arranged at the reservoir 44b located at an end (second end part) in the +X direction of the electrophoresis cell 44. The power source 41 generates a potential difference between the negative electrode 42 and the positive electrode 43. As an example, the power source 41 generates the potential difference between the negative electrode 42 and the positive electrode 43 such that an electric field intensity in the flow path 44c is 50 [V/cm]. A force is applied to a particle in a medium for moving the particle in a predetermined direction (X direction in a case of this example) in the medium. The electrophoresis apparatus 40 is capable of causing a variety of particles to be suspended in a medium and to be migrated. The electrophoresis apparatus 40 of the present embodiment can be used for electrophoresis of a particle. Examples of a particle include an exosome, a lipid vesicle including an apoptosis body, a micro vesicle, or the like, an extracellular vesicle, a latex particle (including a latex particle modified with an antibody and further modified with a cell), a polymer micelle, and the like. The present embodiment is described using an example in which immunoelectrophoresis is applied to an exosome extracted from a body fluid such as blood, saliva, and urine of a cancer patient.

Figure 2:
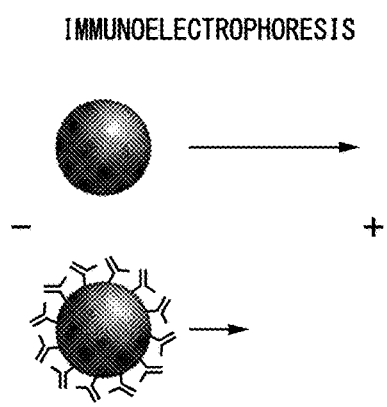
FIG. 2 is a schematic view showing an example of electrophoresis of an exosome and electrophoresis of an antibody-exosome complex.

FIG. 2 is a schematic view showing an example of electrophoresis of an exosome and electrophoresis of an antibody-exosome complex. As shown in FIG. 2, the exosome is negatively charged, while the antibody is positively charged. Therefore, the zeta potential of the antibody-exosome complex has a positive charge compared to the zeta potential of the exosome alone. Accordingly, a migration mobility of the antibody-exosome complex is smaller than a migration mobility of the exosome. In the immunoelectrophoresis, the number of exosomes during electrophoresis is counted, and thereby, a histogram of a zeta potential versus the number of exosome particles is generated.

Figure 3A:
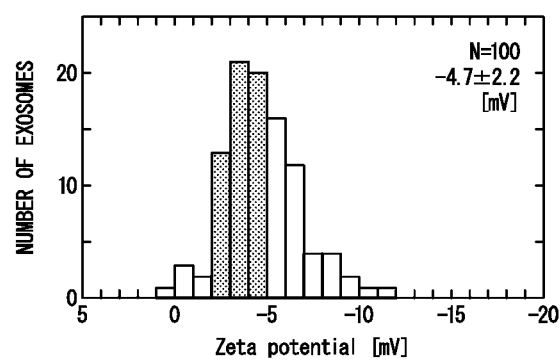
FIG. 3A is a graph showing an example of a histogram of a zeta potential versus the number of exosome particles.
Figure 3B:
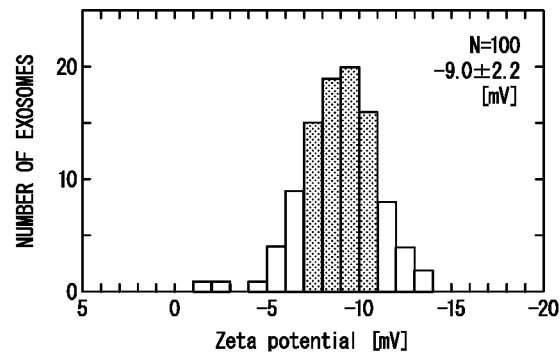
FIG. 3B is a graph showing an example of a histogram of a zeta potential versus the number of exosome particles.

FIGS. 3A and 3B are graphs showing an example of a histogram of a zeta potential versus the number of exosome particles.

In FIG. 3A and FIG. 3B, the horizontal axis represents zeta potential, and the vertical axis represents the number of exosome particles (in the following description, also referred to as the number of exosomes). FIG. 3A shows the distribution of a zeta potential in an exosome suspension. FIG. 3B shows the distribution of a zeta potential in an antibody-exosome suspension. The average value of the zeta potential at some number of exosomes can be obtained from this histogram of a zeta potential versus the number of exosomes. In this example, the average value of the zeta potential in a case where the number of exosomes is 100 is obtained. In the example, as shown in FIG. 3A, the average value of the zeta potential in an exosome suspension is −4.7±2.2 [mV]. Further, as shown in FIG. 3B, the average value of the zeta potential in an antibody-exosome suspension is −9.0±2.2 [mV].

Further, according to this histogram of a zeta potential versus the number of exosomes, it is possible to measure not only the average value of the zeta potential of the antibody-exosome complex but also the zeta potential of the antibody-exosome complex at one particle level. Therefore, even in a case where it is considered that an exosome having an antigen recognized by an antibody is not present in a sample based on the average value of the zeta potential, it is possible to detect the exosome having the antigen, which is present as a minor population, by an electrophoresis chip. By analyzing the histogram of a zeta potential versus the number of exosome particles in this way, for example, it is possible to detect a small amount of highly malignant cancer cells that are present in a living body with high sensitivity and find the infiltration and metastasis of a cancer at an early stage.

Further, it is also possible to compare zeta potentials of a plurality of types of antibody-exosome complexes. As an example, by measuring a zeta potential of a first antibody-exosome complex by using an antibody to be bound to an antigen which is a protein specifically expressed by a cancer cell as a first antibody and subsequently by measuring a zeta potential of a second antibody-exosome complex by using an antibody to be bound to an antigen which is a protein specifically expressed by an organ as a second antibody, it is possible to specify from which organ originates a detection-target cancer cell. Further, the detection-target cell is not limited to a cancer cell, and it is possible to specify in detail an abnormality of a cell in a living body by changing the combination of used antibodies.

This histogram of a zeta potential versus the number of exosomes is generated by detecting a movement path of each exosome moving by electrophoresis in a medium. In order to improve the accuracy of this histogram, it is required to accurately detect the path of an exosome in a medium. Hereinafter, a mechanism for accurately detecting the path of an exosome in a medium is described.

With reference back to FIG. 1, the observation apparatus 1 includes a particle analysis apparatus 2, an imaging unit 10, an irradiation unit 20, and a dark-field optical system 30.

The irradiation unit 20 irradiates a medium in the flow path 44c of the electrophoresis apparatus 40 with illumination light. When particles suspended in the medium in the flow path 44c are irradiated with this illumination light, scattered light occurs.

Here, an example of particles is an exosome described above. In the following description, a case in which an exosome is observed using the observation apparatus 1 is described; however, a particle other than an exosome can also be observed using the observation apparatus 1.

The dark-field optical system 30 includes an objective lens 31 and a dichroic mirror 32.

The objective lens 31 is arranged at a position on which illumination light irradiated by the irradiation unit 20 is not directly incident. Further, scattered light that occurs when an exosome is irradiated with illumination light is incident on the objective lens 31. The dichroic mirror 32 is a reflection-transmission member having a different reflection-transmission characteristic depending on the wavelength of light. The dichroic mirror 32 is arranged on an optical path between the objective lens 31 and the imaging unit 10 and reflects at least part of light that is incident from the objective lens 31 toward the imaging unit 10.

The dark-field optical system 30 includes the objective lens 31 and the dichroic mirror 32 to thereby enable dark-field observation of an observation area DOF in the flow path 44c by the imaging unit 10.

The imaging unit 10 includes an electron-multiplying charge-coupled device (EMCCD) camera and captures an image of incident light. The imaging unit 10 can capture a moving image.

As an example, the imaging unit 10 captures an image at a rate of 100 [frame/sec]. The imaging unit 10 outputs the captured image to the particle analysis apparatus 2. Note that, the imaging unit 10 may include an imaging element such as a CMOS or NMOS other than the EMCCD camera.

The particle analysis apparatus 2 detects the movement path of an exosome based on the image captured by the imaging unit 10. The functional configuration of the particle analysis apparatus 2 is described with reference to FIG. 4.

Figure 4:
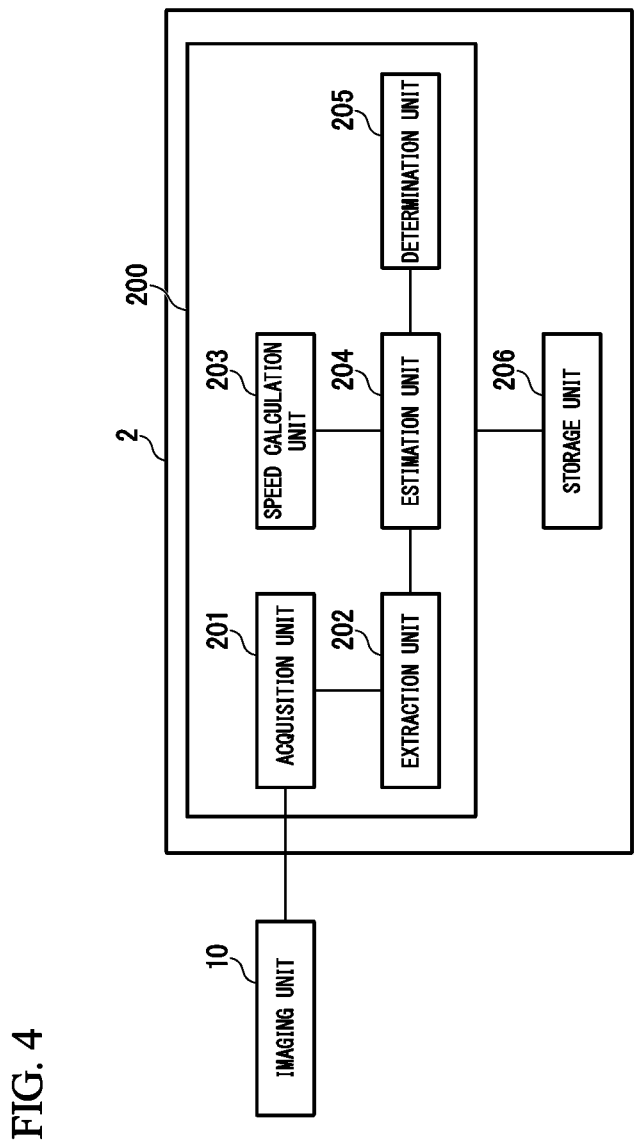
FIG. 4 is a configuration view showing an example of a functional configuration of a particle analysis apparatus of the present embodiment.

FIG. 4 is a configuration view showing an example of the functional configuration of the particle analysis apparatus 2 of the present embodiment.

The particle analysis apparatus 2 includes a calculation unit 200 and a storage unit 206. The storage unit 206 includes a storage device such as a flash memory, a hard disk drive (HDD), a random access memory (RAM), a read-only memory (ROM), and a register. A program (firmware) that is executed by the calculation unit 200 is stored in the storage unit 206 in advance.

Further, a calculation result of a calculation process by the calculation unit 200 is stored in the storage unit 206.

The calculation unit 200 includes a central processing unit (CPU) and performs a variety of calculations. The calculation unit 200 includes an acquisition unit 201, an extraction unit 202, a speed calculation unit 203, an estimation unit 204, and a determination unit 205 as functional units.

The acquisition unit 201 acquires an image captured by the imaging unit 10. As described above, the imaging unit 10 captures a moving image of an exosome that moves in a medium. That is, the acquisition unit 201 acquires a plurality of images in each of which a particle moving in a predetermined direction in a medium is captured at a different time. The acquisition unit 201 outputs the acquired image to the extraction unit 202.

The extraction unit 202 extracts an image of an exosome from the images captured by the imaging unit 10. For example, the extraction unit 202 selects an image of one frame from the images supplied from the acquisition unit 201 and applies a known filter process or pattern-matching process to the selected image to thereby extract an exosome image. At this time, the extraction unit 202 imparts a particle number for each exosome particle to the extracted exosome image. That is, the extraction unit 202 labels the exosome particles. Here, there may be a case in which although an exosome is present in the medium of the flow path 44c, the imaging unit 10 cannot capture an image of the exosome.

Figure 5:
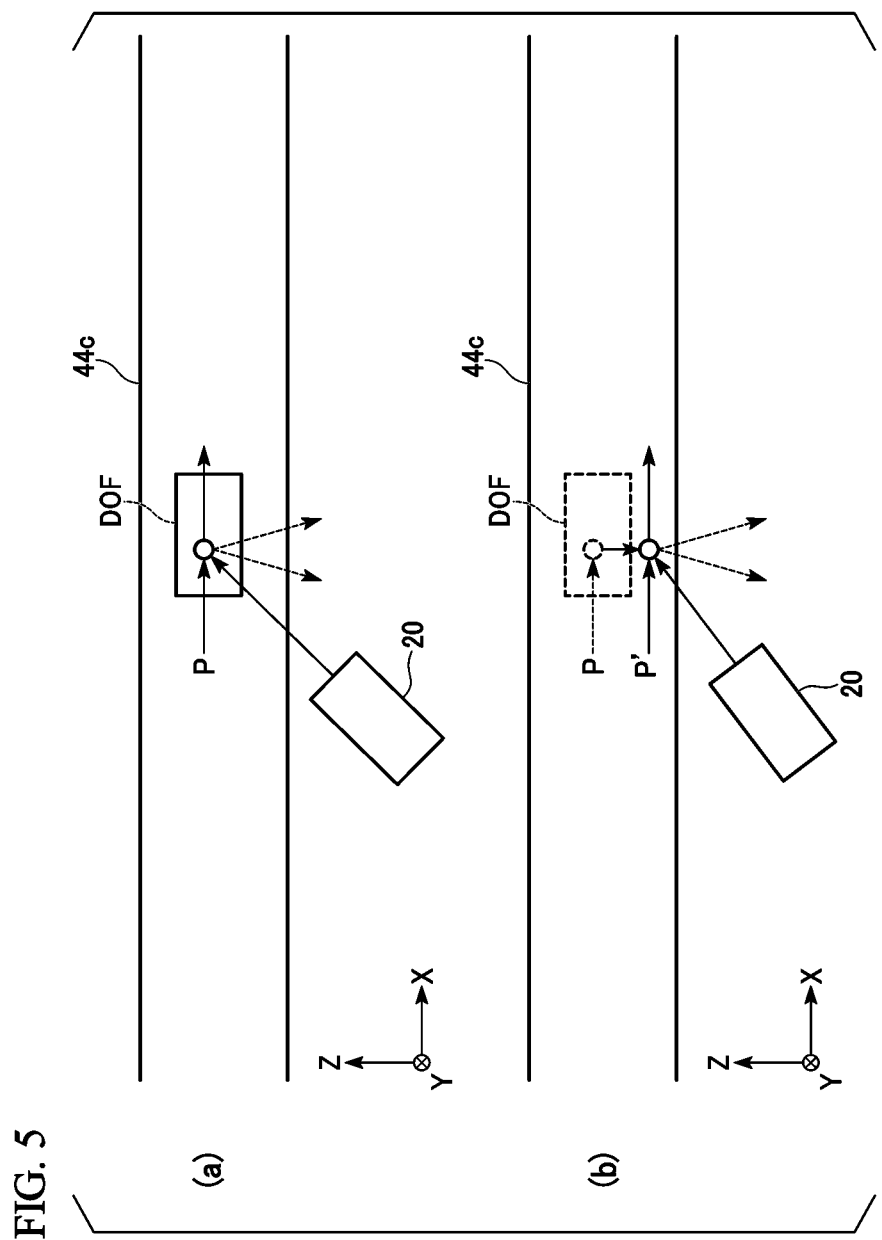
FIG. 5 is a schematic view showing an example of an observation area according to the observation apparatus of the present embodiment.

FIG. 5 is a schematic view showing an example of an observation area DOF according to the observation apparatus 1 of the present embodiment. Part (a) of FIG. 5 shows a case in which an exosome is present at a position P of the observation area DOF in the flow path 44c. As shown in part (a) of FIG. 5, the imaging unit 10 captures an image of a particle that passes through the observation area DOF in the flow path 44c. The exosome travels in the X direction by electrophoresis in the flow path 44c. The irradiation unit 20 irradiates a range including the observation area DOF with light. When the light irradiated by the irradiation unit 20 is incident on an exosome, scattered light occurs. The imaging unit 10 captures an image of the scattered light occurring from the exosome at the position P in the observation area DOF.

Here, the exosome is suspended in the medium and moves due to Brownian motion. Therefore, the exosome may move out of the observation area DOF. Part (b) of FIG. 5 shows a case in which the exosome moves to a position P' in the −Z direction due to Brownian motion.

As shown in part (b) of FIG. 5, when the exosome moves out of the observation area DOF, although the exosome is present, the imaging unit 10 cannot capture an image of the exosome.

Figure 6:
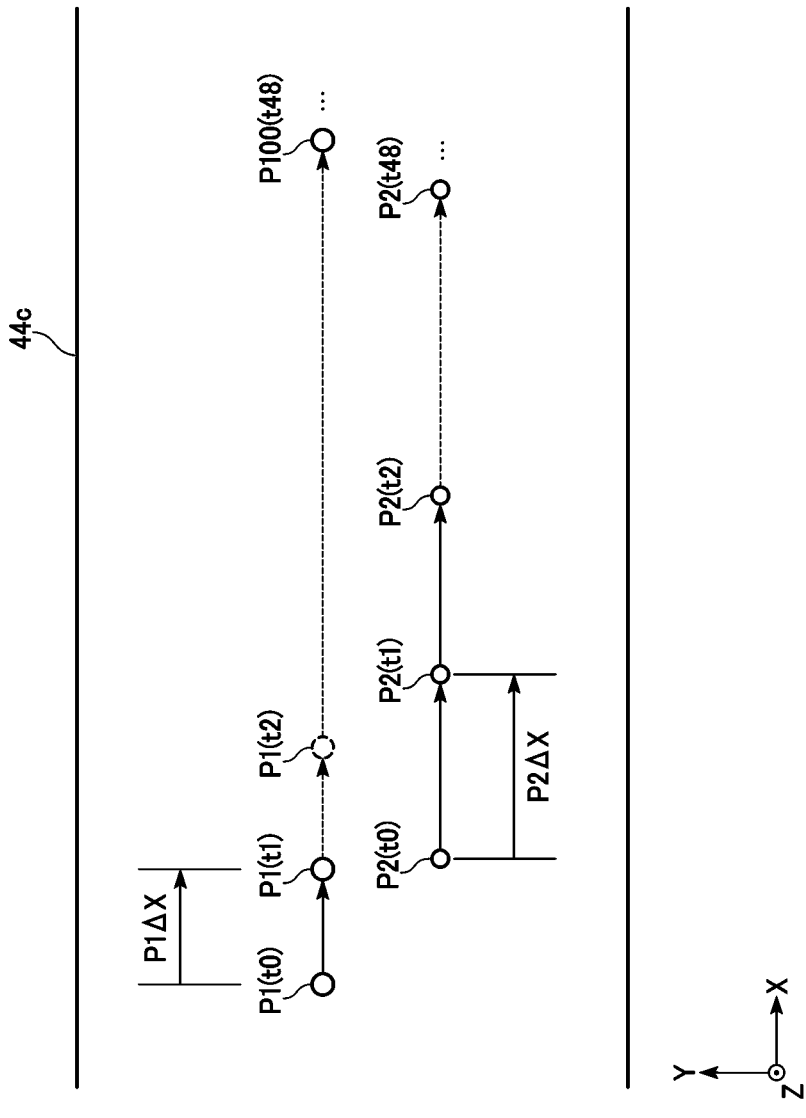
FIG. 6 is a schematic view showing an example of images of an exosome arranged in a time series.

Further, the exosome that once moves out of the observation area DOF may again move to the observation area DOF due to Brownian motion. In this case, the imaging unit 10 can capture an image of the exosome. An example in which images of the exosome are arranged in a time series is described with reference to FIG. 6. FIG. 6 is a schematic view showing an example of images of an exosome arranged in a time series. With reference to FIG. 6, movement paths of two exosomes, which are an exosome P1 and an exosome P2, are described. As described above, the imaging unit 10 captures an image at a predetermined time interval. In this example, the imaging unit 10 captures an image of one frame at each time of time t0 to time t50 at a frequency of 100 [frame/sec]. That is, the imaging unit 10 captures images of 51 frames at an interval of 0.5 sec.

In FIG. 6, for example, a position of the exosome P1 at time t0 is represented by a position P1(t0). Further, for example, a position of the exosome P2 at time t48 is represented by a position P2(t48). As shown in FIG. 6, each exosome moves in the X direction due to electrophoresis as the time elapses. As an example, the exosome P1 moves in the X direction from the position P1(t0) to a position P1(t1) and . . . as the time elapses. Further, the exosome P2 moves in the X direction from the position P2(t0) to the position P2(t1) and . . . as the time elapses.

In this example, the exosome P1 is in the observation area DOF at a time from time t0 to time t1. Further, the exosome P1 is out of the observation area DOF at a time from time t2 to time t47 and returns to the observation area DOF again at time t48. Further, the exosome P2 is in the observation area DOF at a time from time t0 to time t48.

In this example, the exosome P1 and the exosome P2 are imaged in an image captured by the imaging unit 10 at time t0 and time t1. Further, in an image captured by the imaging unit 10 at a time from time t2 to time t47, the exosome P2 is imaged, but the exosome P1 is not imaged. Further, the exosome P1 and the exosome P2 are imaged in an image captured by the imaging unit 10 at time t48.

The extraction unit 202 extracts an exosome image from the image captured by the imaging unit 10 at each time and calculates, based on the extracted exosome image, the coordinate of the exosome and the brightness and area of the exosome image. Further, the extraction unit 202 writes the calculated coordinate of the exosome and the calculated brightness and area of the exosome image in the storage unit 206.

Here, a process of the extraction unit 202 on the image captured at time t0 is described. In an example shown in FIG. 6, the extraction unit 202 extracts two exosome images from the image captured at time t0. The extraction unit 202 labels one of the extracted two exosome images as the exosome P1 and labels the other of the extracted two exosome images as the exosome P2. Further, the extraction unit 202 calculates the coordinate (x1, y1) of the position P1(t0), the brightness l1, and the area s1 of the labeled exosome P1. The extraction unit 202 writes the calculated coordinate (x1, y1), the brightness l1, and the area s1 of the exosome P1 on a particle list stored by the storage unit 206. An example of the particle list stored by the storage unit 206 is described with reference to FIG. 7.

FIG. 7 is a view showing an example of a particle list stored by a storage unit 206 of the present embodiment. The particle list presents the labeled particle number in the row direction and presents the imaging time in the column direction, and the coordinate (X, Y), brightness L, and area S of the image of each particle at each time are stored in the particle list. As an example, the extraction unit 202 writes the calculated coordinate (x1, y1), brightness l1, and area S1 at the column of time t0 at the row of the exosome P1 in the particle list. The extraction unit 202 calculates the coordinate (X, Y), brightness L, and area S at each time and writes the calculated coordinate (X, Y), brightness L, and area S on the particle list also for the exosome P2 similarly to the exosome P1.

With reference back to FIG. 6, a process of the extraction unit 202 on the image captured at time t1 is described. The extraction unit 202 extracts two exosome images from the image captured at time t1. The extraction unit 202 determines whether or not one of the extracted two exosome images has continuity with each exosome image captured at time t0. For example, the extraction unit 202 determines whether or not images captured at two different times have continuity with each other as described below.

The extraction unit 202 compares the coordinate of the exosome captured at time t1 and the coordinates of the exosomes captured at time t0. Here, since the exosome moves in the X direction due to electrophoresis, a relatively large displacement occurs in the X direction. Further, the displacement of the exosome in the Y direction is smaller than the displacement in the X direction. Therefore, the extraction unit 202 determines that an exosome having a Y coordinate that is close to the Y coordinate (y1) of the exosome captured at time t2 of Y coordinates of the exosomes captured at time t0 has continuity. For example, the extraction unit 202 compares the Y coordinate (y1) of an exosome captured at time t1 to the Y coordinate (y1) of the exosome P1 captured at time t0. Further, the extraction unit 202 compares the Y coordinate (y1) of the exosome captured at time t1 to the Y coordinate (y2) of the exosome P2 captured at time t0. In this example, the Y coordinate (y1) of the exosome captured at time t1 is closer to the Y coordinate (y1) of the exosome P1 than the Y coordinate (y2) of the exosome P2. Therefore, the extraction unit 202 determines that the image of the exosome captured at time t2 has continuity with the image of the exosome P1 captured at time t0.

In this case, the extraction unit 202 labels the image of the exosome captured at time t1 as the exosome P1. Further, the extraction unit 202 writes the coordinate (x1', y1), brightness l1, and area S1 at time t1 of the exosome P1 at the column of time t1 at the row of the exosome P1 in the particle list.

Further, the extraction unit 202 determines continuity with the last frame similarly with respect to another exosome captured at time t1 also and performs labeling.

Here, a process of the extraction unit 202 on the image captured at time t48 is described. The extraction unit 202 extracts two exosome images from the image captured at time t48. The extraction unit 202 determines whether or not one of the extracted two exosome images has continuity with the exosome image captured at time t47 just before time t48. As described above, the exosome P1 is not imaged in the image captured by the imaging unit 10 at time t47. That is, an exosome that can be labeled as the exosome P1 at time t48 is not imaged in the image captured by the imaging unit 10 at time t47. The extraction unit 202 does not label any of the exosomes captured at time t48 as the exosome P1. The extraction unit 202 labels the exosome that is not labeled as the exosome P1, as a new exosome. In this example, the extraction unit 202 labels the exosome as an exosome P100.

Note that, in this example, the extraction unit 202 determines the continuity of images by comparing Y coordinates of exosomes; however, the extraction unit 202 may extract exosome images and determine the continuity of images by comparing brightness or area of exosome images. Further, the extraction unit 202 may extract exosome images and determine the continuity of images by combining at least two of the Y coordinate, brightness and area and comparing the combinations. That is, the extraction unit 202 may extract exosome images and determine the continuity of images based on the particle size of exosomes.

Hereinbefore, a process in which an exosome image is labeled in the images of two frames is described. Next, a process in which it is determined whether or not the exosome images to which a different particle number is imparted are images indicating the same exosome is described. At this time, the determining that the images are images indicating the same exosome means replacing, when an exosome to which a particle number 1 is imparted at one time is imparted by a particle number 2 at another time, the particle number of the exosome to which the particle number 2 is imparted by the particle number 1. For example, the exosomes to which different particle numbers are imparted are labeled again and are imparted by the same particle number. As an example, a case in which it is determined whether or not the exosome P100 described above is the same as the exosome P1 is described.

The speed calculation unit 203 calculates the movement speed of an exosome based on the coordinate of the exosome calculated by the extraction unit 202 and the difference between imaging times. As described above, the extraction unit 202 calculates the coordinate (x1, y1) at time t0 and the coordinate (x1', y1) at time t1 of the exosome P1. Further, as described above, the imaging unit 10 captures an image of one frame at each time from time t0 to time t50 at a frequency of 100 [frame/sec]. Accordingly, in this example, a time from time t0 to time t1, that is, a time between adjacent frames is 0.01 sec. The speed calculation unit 203 acquires the X coordinate (x1) at time t0 and the X coordinate (x1') at time t1 calculated by the extraction unit 202 of the exosome P1. Further, the speed calculation unit 203 calculates a difference P1ΔX between the acquired X coordinates of the exosome P1 and divides the calculated difference P1ΔX between the X coordinates by the time between frames to thereby calculate a movement speed v1 of the exosome P1. In this way, the speed calculation unit 203 calculates the movement speed of the movement in a predetermined direction of the exosome P1 from a plurality of images.

The estimation unit 204 estimates the coordinate of the exosome after a time elapses based on the movement speed of the exosome calculated by the speed calculation unit 203. Here, when the X coordinate (x1) of the exosome P1 at time t0 and the movement speed v1 of the exosome P1 are known, the X coordinate (xT1) of the exosome P1 when a time T1 elapses since time t0 can be obtained by Expression (1).

$$xT1=x1+v1\times T1 \tag{1}$$

The estimation unit 204 acquires the X coordinate (x1) of the exosome P1 at time t0 calculated by the extraction unit 202 and the X coordinate (x100) of the exosome P100 at time t48 calculated by the extraction unit 202. Further, the estimation unit 204 acquires the movement speed v1 of the exosome P1 calculated by the speed calculation unit 203. Here, the time T1 is a time from time t0 to time t48. In this example, the time T1 is 0.48 sec. The estimation unit 204 substitutes the acquired parameters for above-described Expression (1) and calculates the X coordinate (xT1) of the exosome P1 at time t48. In this way, the estimation unit 204 estimates the coordinate of the exosome P1 at time t48 based on the coordinate at time t0 of the exosome P1 and the movement speed v1 of the movement in the X direction of the exosome P1.

The determination unit 205 determines whether or not the exosomes imaged at two times are the same as each other based on the coordinates of the exosomes estimated by the estimation unit 204. For example, the determination unit 205 acquires the X coordinate (x100) of the exosome P100 at time t48 calculated by the extraction unit 202 and the X coordinate (xT1) of the exosome P1 at time t48 estimated by the estimation unit 204. Further, the determination unit 205 compares the acquired X coordinate (x100) of the exosome P100 to the acquired X coordinate (xT1) of the exosome P1. Here, the determination unit 205 tentatively determines that the exosome P100 is the same as the exosome P1 when the difference between the X coordinate (x100) of the exosome P100 and the X coordinate (xT1) of the exosome P1 is a predetermined threshold value or less.

Further, when the determination unit 205 tentatively determines that the exosome P100 is the same as the exosome P1, the determination unit 205 performs a process of conclusive determination based on the difference between Y coordinates of the exosomes. For example, the determination unit 205 acquires the Y coordinate (y1) of the exosome P1 at time t0 calculated by the extraction unit 202 and the Y coordinate (y100) of the exosome P100 at time t48 calculated by the extraction unit 202.

As described above, an exosome is suspended in a medium and moves in a variety of directions due to Brownian motion. Therefore, the exosome not only moves in the X direction due to electrophoresis but also may move in the Y direction due to Brownian motion. The determination unit 205 conclusively determines whether or not the exosome P1 at time t0 is the same as the exosome P100 at time t48 based on an allowable value BM of the movement amount of the movement of the exosome in the Y direction due to Brownian motion. For example, the determination unit 205 calculates a difference Δy between the acquired Y coordinate (y1) of the exosome P1 at time t0 and the acquired Y coordinate (y100) of the exosome P100 at time t48. Further, the determination unit 205 compares the calculated difference Δy between the Y coordinates to the allowable value BM and, when the difference Δy between the Y coordinates is the allowable value BM or less, conclusively determines that the exosome P1 at time t0 is the same as the exosome P100 at time t48. That is, the determination unit 205 conclusively determines whether or not the exosomes are the same as each other based on at least a component in the Y direction that is perpendicular to the X direction, which is the movement direction due to electrophoresis of components of the movement amount of the exosome due to Brownian motion.

The determination unit 205 determines, based on the exosome movement amount due to Brownian motion in the medium, whether or not the exosome P1 imaged at time t0 of a plurality of images acquired by the acquisition unit 201 and the exosome P100 imaged at time t48 of the plurality of images acquired by the acquisition unit 201 are the same as each other.

Note that, the embodiment is described using an example in which the determination unit 205 determines whether or not the exosome images at two times indicate the same exosome based on the exosome movement amount in the Y direction due to Brownian motion; however, the embodiment is not limited thereto. The determination unit 205 may determine whether or not the exosome images at two times indicate the same exosome based on the movement amount due to Brownian motion with respect to the X direction which is the electrophoresis direction. That is, when the exosome moves in the X direction due to Brownian motion, the determination unit 205 may determine whether or not the exosome images at two times indicate the same exosome based on the allowable value of the exosome displacement due to Brownian motion in the X direction. Further, the determination unit 205 may determine whether or not the exosome images at two times indicate the same exosome by combining movement amounts due to Brownian motion in the X direction and the Y direction.

Next, the operation of the particle analysis apparatus 2 is described with reference to FIG. 8.

Figure 8:
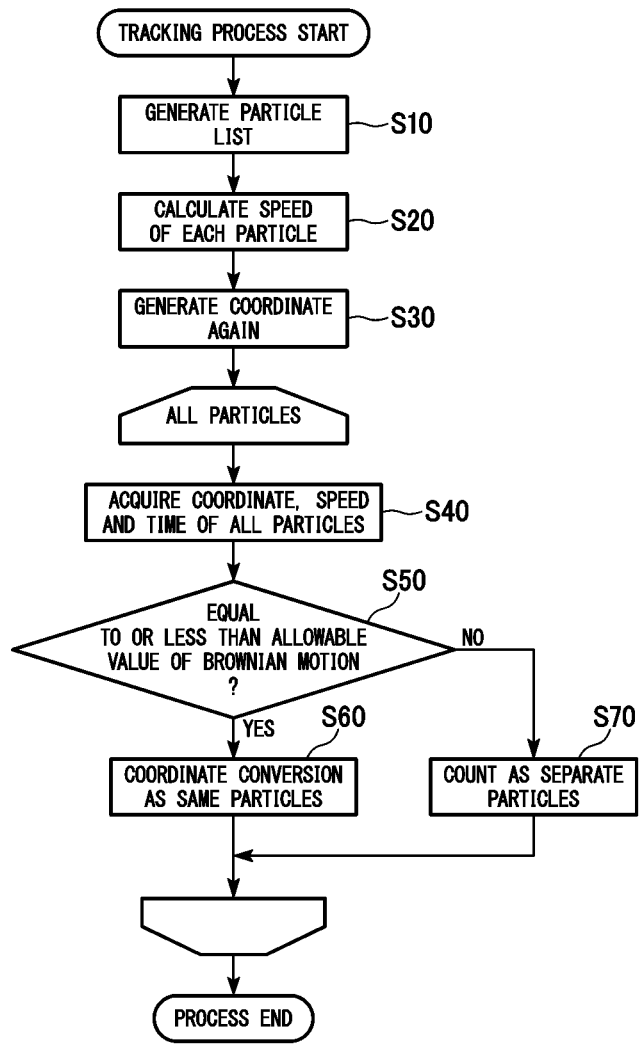
FIG. 8 is a flowchart showing an example of an operation of the particle analysis apparatus of the present embodiment.

FIG. 8 is a flowchart showing an example of the operation of the particle analysis apparatus 2 of the present embodiment.

The extraction unit 202 generates a particle list (step S10). For example, the extraction unit 202 extracts an exosome image from the images captured by the imaging unit 10 at each time and calculates, based on the extracted exosome image, the coordinate of the exosome and the brightness and area of the exosome image. Further, the extraction unit 202 writes the calculated coordinate of the exosome and the calculated brightness and area of the exosome image on the particle list in the storage unit 206.

Next, the speed calculation unit 203 calculates the movement speed of the exosome based on the coordinate of the exosome calculated by the extraction unit 202 and the difference between imaging times (step S20).

Next, the extraction unit 202 performs coordinate conversion for converting coordinate values stored in the particle list of the storage unit 206 into the electrophoresis direction (X direction in this example) to generate the coordinates again (step S30). Thereby, even when the electrophoresis direction does not match the imaging direction of the imaging unit 10 and the exosome is imaged so as to move in a direction other than the X direction, the particle analysis apparatus 2 can accurately track the exosome.

Next, the processes from step S40 to step S70 are repeatedly applied on all the exosomes extracted by the extraction unit 202.

First, the determination unit 205 acquires the imaging interval. Further, the determination unit 205 acquires a coordinate at a first time, a coordinate at a second time, and a movement speed of the focused exosome (step S40).

Next, when the difference between the X coordinate at the first time of the focused exosome and the X coordinate at the second time of the focused exosome is a predetermined threshold value or less, the determination unit 205 tentatively determines that the exosomes at these two times are the same as each other. Next, when the difference between the Y coordinates of the two exosomes that are tentatively determined to be the same is the predetermined threshold value or less, the determination unit 205 conclusively determines that the two exosomes are the same as each other. Here, when the calculated difference between the Y coordinates is equal to or less than the allowable value BM due to Brownian motion (step S50; YES), the determination unit 205 advances the process to step S60. On the other hand, when the calculated difference between the Y coordinates exceeds the allowable value BM due to Brownian motion (step S50; NO), the determination unit 205 advances the process to step S70.

Next, in step S60, the determination unit 205 performs labeling such that the two exosomes are the same as each other. On the other hand, in step S70, the determination unit 205 performs labeling such that the two exosomes are different from each other.

The determination unit 205 applies the processes from step S40 to step S70 repeatedly on all the exosomes extracted by the extraction unit 202 and then ends the process.

As described above, as the particle analysis apparatus 2 includes the determination unit 205, when there is a time during which the exosome cannot be imaged, the particle analysis apparatus 2 can determine whether or not the exosomes imaged at separate times are the same as each other. Accordingly, the particle analysis apparatus 2 can prevent the number of exosomes from being erroneously measured due to one exosome being determined as separate exosomes in the image processing. That is, according to the particle analysis apparatus 2, it is possible to reduce the measurement error of a particle.

Further, the particle analysis apparatus 2 applies, to a particle, a force that moves the particle in a predetermined direction. For example, the particle analysis apparatus 2 applies, to a particle, an electric field that moves the particle in the X direction described above. Thereby, the particle moves on a path determined by a movement amount due to an electric field and a movement amount due to Brownian motion. The particle analysis apparatus 2 estimates the position of the particle in consideration of the movement amount due to Brownian motion and thereby can estimate the movement path of the particle. At this time, when the movement amount due to Brownian motion is smaller than the movement amount due to the electric field, the particle analysis apparatus 2 can further accurately estimate the position of the particle.

That is, when the movement amount due to Brownian motion is smaller than the movement amount due to the electric field, the particle analysis apparatus 2 can further reduce the measurement error of a particle.

[Second Embodiment]

Hereinafter, a second embodiment of the present invention will be described with reference to the drawings. Note that, the same reference numerals are given to the configurations and operations that are the same as those of the first embodiment described above, and the description thereof will be simplified or omitted. The observation apparatus 1a of the present embodiment is different from that of the first embodiment in that the irradiation unit 20 irradiates the flow path 44c with light via a ring band 50.

Figure 9:
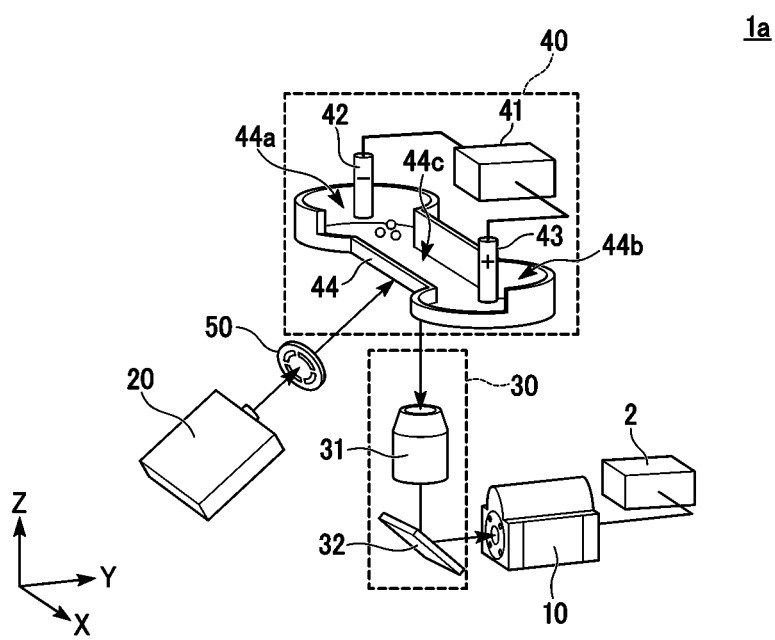
FIG. 9 is a schematic view showing an example of a configuration of an observation apparatus of a second embodiment of the present invention.

FIG. 9 is a schematic view showing an example of a configuration of the observation apparatus 1a of the second embodiment of the present invention. The observation apparatus 1a includes the ring band 50. The irradiation unit 20 irradiates the flow path 44c via the ring band 50 with light from a light source. The configuration of the ring band 50 is described with reference to FIG. 10.

Figure 10:
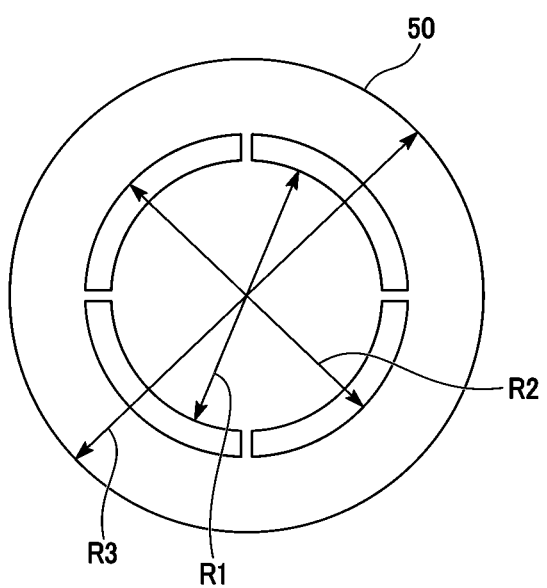
FIG. 10 is a schematic view showing an example of a configuration of a ring band of the present embodiment.

FIG. 10 is a schematic view showing an example of a configuration of the ring band 50 of the present embodiment. The ring band 50 has an inner shielding part having a diameter R1 and an outer shielding part having a diameter R3. The ring band 50 has a transmission part between the inner shielding part and the outer shielding part. The transmission part is provided in a range from the diameter R1 to a diameter R2. The ratio (ring band ratio) of the diameter R1 of an inner ring of the transmission part to the diameter R2 of an outer ring of the transmission part is changed, and thereby, the ring band 50 changes illumination properties by transmitted light. The ring band ratio is obtained by dividing the diameter R1 by the diameter R2. In the present embodiment, the ring band ratio of the ring band 50 can be 0.8 to 0.85. The numerical value is an example, and the ring band ratio is not limited thereto.

Figure 11:
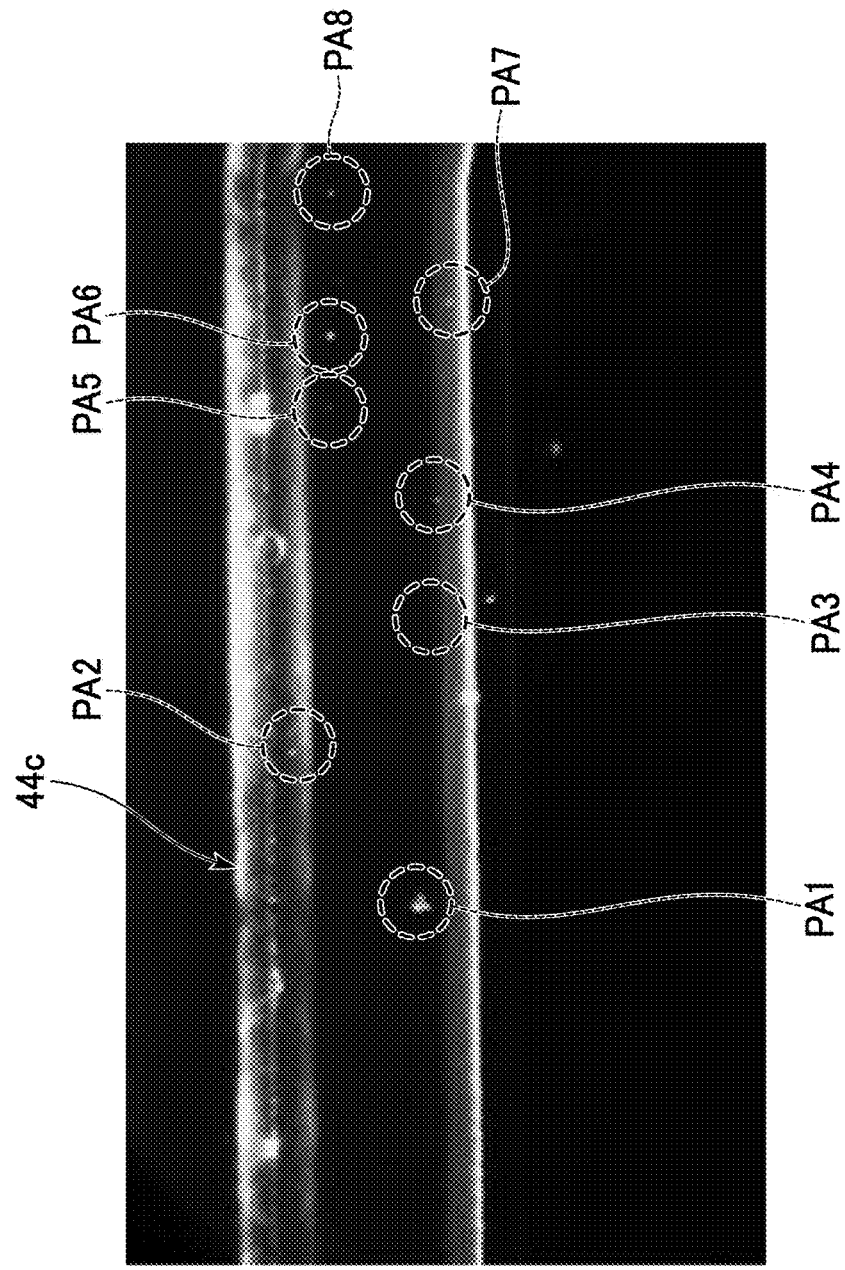
FIG. 11 is a schematic view showing an example of an observation result of a particle according to the observation apparatus of the present embodiment.

FIG. 11 is a schematic view showing an example of an observation result of a particle according to the observation apparatus 1a of the present embodiment. The observation apparatus 1a illuminates the flow path 44c via the ring band 50. Therefore, according to the observation apparatus 1a, for example, it is possible to reduce scattered light when light is incident on the flow path 44c compared to a case where the flow path 44c is directly irradiated with laser light. Further, by setting the ring band ratio of the ring band 50 in the above-described range, it is possible to improve the contrast of the image captured by the imaging unit 10 while reducing the scattered light by the flow path 44c. Therefore, according to the observation apparatus 1a, since particles PA1 to PA8 can be imaged at high contrast as shown in FIG. 11, it is possible to reduce the measurement error of a particle.

Figure 12:
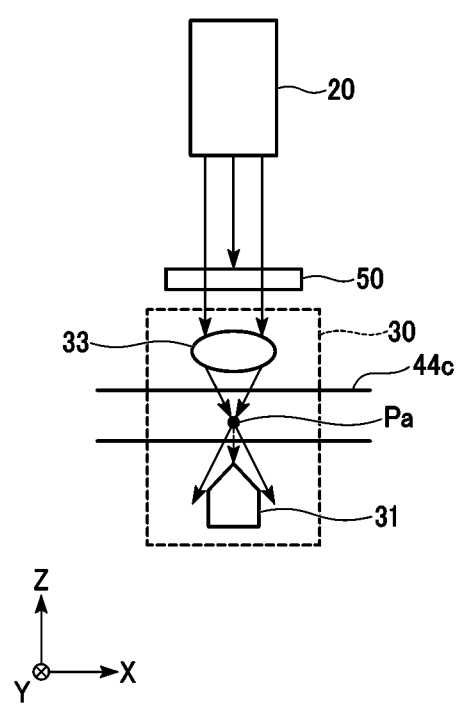
FIG. 12 is a schematic view showing a modified example of a dark-field optical system of the observation apparatus.

Note that, the observation apparatus 1a may be configured as shown in FIG. 12.

FIG. 12 is a schematic view showing a modified example of a dark-field optical system of the observation apparatus 1a. As shown in FIG. 12, the dark-field optical system 30 according to the modified example includes a lens 33. The lens 33 focuses incident light via the ring band 50 from the irradiation unit 20 at a position of the observation area DOF in the flow path 44c. In a case where a particle Pa is present in the flow path 44c, when the light focused by the lens 33 is incident on the particle Pa, scattered light occurs. The objective lens 31 is arranged at a position on which the light focused by the lens 33 is not directly incident and on which the scattered light is incident. Even according to such a configuration, the observation apparatus 1a can perform dark-field observation of a particle in the flow path 44c.

Note that, in the observation apparatus 1 (or observation apparatus 1a, same in the following description) according to the embodiments described above, a case in which a particle is moved in a predetermined direction by electrophoresis is described; however, the configuration is not limited thereto. For example, the observation apparatus 1 may move a particle in a predetermined direction by applying a flow rate to the medium. Further, the observation apparatus 1 may be configured not to apply a force that moves a particle in a predetermined direction.

Part of the observation apparatus 1 in the embodiments described above may be realized by a computer. In this case, a program for realizing the control function may be recorded in a computer-readable recording medium, and the program recorded on the recording medium may be read into a computer system and executed to realize the control function. The "computer system" used herein is assumed to be a computer system embedded in the observation apparatus 1 and including an OS and hardware such as peripherals. Further, the "computer-readable recording medium" refers to a portable medium such as a flexible disk, a magneto-optical disk, a ROM and a CD-ROM or a storage device such as a hard disk embedded in the computer system. Furthermore, the "computer-readable recording medium" may also include a medium which dynamically holds a program for a short period of time such as a communication line when the program is transmitted through a network such as the Internet or a communication network line such as a telephone network line, and a medium which holds the program for a given period of time such as a volatile memory in a computer system which serves as a server or a client. The program described above may be a program which realizes part of the functions described above. The functions described above may be realized in combination with a program having already been recorded in the computer system. Further, part or all of the functional blocks of the observation apparatus 1 in the embodiments described above may be realized as an integrated circuit such as large scale integration (LSI). Each one of the functional blocks of the observation apparatus 1 may be individually realized in the form of a processor, or part or all of the functional blocks may be integrated in the form of a processor. A circuit integration technique is not limited to LSI and may be realized in the form of a dedicated circuit or a general-purpose processor.

When the advance of a semiconductor technology allows advent of a circuit integration technique which replaces LSI, an integrated circuit based on the technology may be used.

Although an embodiment of the invention has been described in detail referring to the drawings, a specific configuration is not limited thereto, and various design changes and the like can be made without departing from the scope of the invention. Further, the configurations shown in the embodiments described above and the modified example may be appropriately combined.

What is claimed is:

1. A particle analysis apparatus, comprising:
a processor and a memory, wherein a plurality of executable program units including an acquisition unit, a determination unit, and an estimation unit are stored in the memory, which are executable by the processor, wherein,
the acquisition unit is executed to acquire a plurality of images each captured at a different time in each of which a particle moving in a predetermined direction in a medium is imaged;
the determination unit is executed to determine, based on a movement amount of a particle due to Brownian motion in the medium, whether or not an image of a first particle included in an image captured at a first time of the plurality of images acquired by the acquisition unit and an image of a second particle included in an image captured at a second time which is different from the first time of the plurality of images acquired by the acquisition unit are images indicating the same particle; and
the estimation unit is executed to estimate a coordinate of the first particle at the second time based on a coordinate at the first time of the first particle indicated by the image of the first particle and a movement speed in the predetermined direction of the first particle;
wherein the determination unit further determines, based on a coordinate at the second time of the second particle indicated by the image of the second particle and the coordinate of the first particle estimated by the estimation unit, whether or not the image of the first particle and the image of the second particle are images indicating the same particle.

2. The particle analysis apparatus according to claim 1, wherein
the determination unit determines that the image of the first particle and the image of the second particle are images indicating the same particle when a difference between the coordinate at the second time of the particle indicated by the image of the second particle and the coordinate of the first particle at the second time estimated by the estimation unit is equal to or less than a movement amount of the first particle due to Brownian motion.

3. The particle analysis apparatus according to claim 1, wherein
a force that moves the particle in the predetermined direction in the medium is applied to the particle.

4. The particle analysis apparatus according to claim 3, wherein
the force that moves the particle is a force due to an electric field applied in the medium.

5. The particle analysis apparatus according to claim 1, wherein
the determination unit determines whether or not the image of the first particle and the image of the second particle are images indicating the same particle based on, among components of a movement amount of the particle due to Brownian motion, at least a component in a direction that is perpendicular to the predetermined direction.

6. The particle analysis apparatus according to claim 1, wherein
the determination unit determines whether or not the image of the first particle and the image of the second particle are images indicating the same particle based on, among components of a movement amount of the particle due to Brownian motion, at least a component in the predetermined direction.

7. The particle analysis apparatus according to claim 1, wherein the plurality of program units further includes a speed calculation unit stored in the memory which is executable by the processor, wherein
the speed calculation unit is executed to calculate the movement speed in the predetermined direction of the first particle from the plurality of images.

8. The particle analysis apparatus according to claim 1, wherein
the particle is an exosome.

9. The particle analysis apparatus according to claim 1, wherein the executable program units further include an extraction unit, wherein,
the extraction unit is executed to extract the image of the first particle from the image captured at the first time and extract the image of the second particle from the image captured at the second time based on a brightness and area of an image of a particle included in an image acquired by the acquisition unit.

10. An observation apparatus, comprising:
the particle analysis apparatus according to claim 1; and
an imaging unit including a camera configured to capture an image of scattered light arising from a particle in the medium due to irradiated light at each one of a plurality of different times.

11. The observation apparatus according to claim 10, comprising:
an irradiation unit configured to irradiate the medium via a ring band with light from a light source.

12. A particle analysis apparatus, comprising:
a processor and a memory, wherein a plurality of executable program units including an acquisition unit, a determination unit, and an estimation unit are stored in the memory, which are executable by the processor, wherein,
the acquisition unit is executed to acquire a plurality of images each captured at a different time in each of which a particle moving in a predetermined direction in a medium is imaged;
the determination unit is executed to determine, based on a coordinate of a first particle included in an image captured at a first time of the plurality of images acquired by the acquisition unit, a coordinate of a second particle included in an image captured at a second time which is different from the first time of the plurality of images acquired by the acquisition unit, and a movement amount of a particle due to Brownian motion in the medium, whether or not the first particle and the second particle are treated as the same particle; and
the estimation unit is executed to estimate a coordinate of the first particle at the second time based on the coordinate of the first particle included in the image captured at the first time and a movement speed in the predetermined direction of the first particle; wherein
the determination unit further determines, based on the coordinate of the second particle included in the image captured at the second time and the coordinate of the first particle estimated by the estimation unit, whether or not the image of the first particle and the image of the second particle are images indicating the same particle.

13. A particle analysis program for causing a computer to execute
(a) acquiring a plurality of images each captured at a different time in each of which a particle moving in a predetermined direction in a medium is imaged;
(b) determining, based on a movement amount of a particle due to Brownian motion in the medium, whether or not an image of a first particle captured at a first time of the plurality of images acquired in (a) and an image of a second particle captured at a second time which is different from the first time of the plurality of images acquired in (a) are images indicating the same particle;
(c) estimating a coordinate of the first particle at the second time based on a coordinate at the first time of the first particle indicated by the image of the first particle and a movement speed in the predetermined direction of the first particle; and
(d) determining, based on a coordinate at the second time of the second particle indicated by the image of the second particle and the coordinate of the first particle estimated by the estimating step, whether or not the image of the first particle and the image of the second particle are images indicating the same particle,
wherein the image of the first particle and the image of the second particle are images indicating the same particle when a difference between the coordinate at the second time of the particle indicated by the image of the second particle and the estimated coordinate of the first particle at the second time is equal to or less than a movement amount of the first particle due to Brownian motion.

14. A particle analysis program for causing a computer to execute
(a) acquiring a plurality of images each captured at a different time in each of which a particle moving in a predetermined direction in a medium is imaged; and
(b) determining, based on a coordinate of a first particle captured at a first time of the plurality of images acquired in (a), a coordinate of a second particle captured at a second time which is different from the first time of the plurality of images acquired in (a), and a movement amount of a particle due to Brownian motion in the medium, whether or not the first particle and the second particle are treated as the same particle;
wherein the first particle and the second particle are treated as the same particle when a difference between the coordinate at the second time of the second particle and an estimated coordinate of the first particle at the second time is equal to or less than the movement amount of the first particle due to Brownian motion,
wherein the estimated coordinate of the first particle at the second time is based on the coordinate at the first time of the first particle and a movement speed in the predetermined direction of the first particle.

15. A particle analysis method, comprising
(a) acquiring a plurality of images each captured at a different time in each of which a particle moving in a predetermined direction in a medium is imaged; and
(b) determining, based on a movement amount of a particle due to Brownian motion in the medium, whether or not an image of a first particle captured at a first time of the plurality of images acquired in (a) and an image of a second particle captured at a second time which is different from the first time of the plurality of images acquired in (a) are images indicating the same particle;
(c) estimating a coordinate of the first particle at the second time based on a coordinate at the first time of the first particle indicated by the image of the first particle and a movement speed in the predetermined direction of the first particle; and
(d) determining, based on a coordinate at the second time of the second particle indicated by the image of the second particle and the coordinate of the first particle estimated by the estimating step, whether or not the image of the first particle and the image of the second particle are images indicating the same particle,
wherein the image of the first particle and the image of the second particle are images indicating the same particle when a difference between the coordinate at the second time of the particle indicated by the image of the second particle and the estimated coordinate of the first particle at the second time is equal to or less than a movement amount of the first particle due to Brownian motion.

16. The particle analysis method according to claim 15, further comprising:
(e) irradiating the medium via a ring band with light from a light source and
(f) capturing an image of scattered light arising from a particle in the medium due to light irradiated in (e) at each one of a plurality of different times, wherein
a plurality of images captured in (f) are acquired in (a).

17. A particle analysis method, comprising
(a) acquiring a plurality of images each captured at a different time in each of which a particle moving in a predetermined direction in a medium is imaged; and
(b) determining, based on a coordinate of a first particle captured at a first time of the plurality of images acquired in (a), a coordinate of a second particle captured at a second time which is different from the first time of the plurality of images acquired in (a), and a movement amount of a particle due to Brownian motion in the medium, whether or not the first particle and the second particle are treated as the same particle,
wherein the first particle and the second particle are treated as the same particle when a difference between the coordinate at the second time of the second particle and an estimated coordinate of the first particle at the second time is equal to or less than the movement amount of the first particle due to Brownian motion,
wherein the estimated coordinate of the first particle at the second time is based on the coordinate at the first time of the first particle and a movement speed in the predetermined direction of the first particle.

* * * * *